United States Patent
Lin (12)

(10) Patent No.: US 6,663,636 B1
(45) Date of Patent: Dec. 16, 2003

(54) FEMUR RASP FASTENER

(75) Inventor: Jason Lin, Hsinchu (TW)

(73) Assignee: United Orthopedic Corporation (TW)

( * ) Notice: Subject to any disclaimer, the term of this patent is extended or adjusted under 35 U.S.C. 154(b) by 0 days.

(21) Appl. No.: 10/095,063

(22) Filed: Mar. 12, 2002

(51) Int. Cl.⁷ .............................. A61F 5/00; A61F 2/00; G05G 1/08
(52) U.S. Cl. .............................. 606/87; 606/79; 606/85; 74/544
(58) Field of Search .............................. 606/85, 86, 87, 606/88, 79, 84, 80, 176, 91, 99, 100, 104; 623/16, 23; 74/544, 524, 543, 546, 547, 548

(56) References Cited

U.S. PATENT DOCUMENTS

| | | | | |
|---|---|---|---|---|
| 5,190,549 A | * | 3/1993 | Miller et al. | 606/85 |
| 5,324,293 A | * | 6/1994 | Rehmann | 606/85 |
| 5,531,750 A | * | 7/1996 | Even-Esh | 606/79 |
| 6,205,884 B1 | * | 3/2001 | Foley et al. | 74/544 |
| 6,478,801 B1 | * | 11/2002 | Ralph et al. | 606/99 |

* cited by examiner

Primary Examiner—Eduardo C. Robert
Assistant Examiner—David A Bonderer
(74) Attorney, Agent, or Firm—Birch, Stewart, Kolasch & Birch, LLP

(57) ABSTRACT

A femur rasp fastener has a frame and a linkage. The frame has a chamber for housing the linkage. When a femur rasp is engaged with the frame and a handle of the linkage is moved, an arched and elastic suspension bar will be driven to pull a bucking hear which is engaged with a front end of the suspension bar so that the bucking head will clamp a strut in an indented recess located at one end of the femur rasp. The femur rasp thus will be held securely and continuously by the frame of the fastener.

5 Claims, 4 Drawing Sheets

FEMUR RASP FASTENER

BACKGROUND OF THE INVENTION

The present invention relates to an improved femur rasp fastener for clamping a femur rasp securely during medical operations to prevent the femur rasp from loosening or breaking away.

Regard femur rasp fasteners, there is a prior art which includes a frame, a linkage means and a bucking means. The frame has a chamber formed therein to house the linkage means and an anchor opening formed at a front end. The anchor opening has a bucking bar located therein to buck against the femur rasp. The chamber has an action zone communicating with the anchor opening and two side walls which have respectively a corresponding anchor zone adjacent to a notch of a bucking means. The frame has another end formed a hitting section which has a screw bore running through the frame and notch. A screw bolt is engaged with the screw bore. The bucking means includes an elastic bar or strip formed in an arched shape and one end with two sides formed respectively a recess section. The recess section forms a fasten section held in one end of the chamber. The fasten section has one side which has an adjustment element located thereon for adjusting the bucking pressure.

While the prior art set forth above may overcome the tolerance problem by adjusting the adjustment element, however when the doctor hits the frame at the hitting section during operation, a vibration will incur. As a result, the adjustment element might get loosened and produce a gap between the operation mechanism and the femur rasp. It could cause troubles for operations.

SUMMARY OF THE INVENTION

The primary object of the present invention is to resolve the foregoing disadvantages of loosening of the adjustment element and forming of gap and tolerance resulting from vibration and hitting on the frame. The invention provides an improved structure that has a linkage means with an elastic suspension arm to engage with a bucking head at a front end, and is capable of bucking an indented recess of a fasten strut to fasten the femur rasp securely with elastic force. Such a construction provides a compensation effect to the instantaneous vibration. As a result, the femur rasp may be fastened to the frame securely under a continuous clamping force. When the doctor hits the fastener during operation, the vibrations incurred won't cause the femur rasp loosening off or breaking away from the fastener.

The foregoing, as well as additional objects, features and advantages of the invention will be more readily apparent from the following detailed description, which proceeds with reference to the accompanying drawings.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENT

Figure 1:
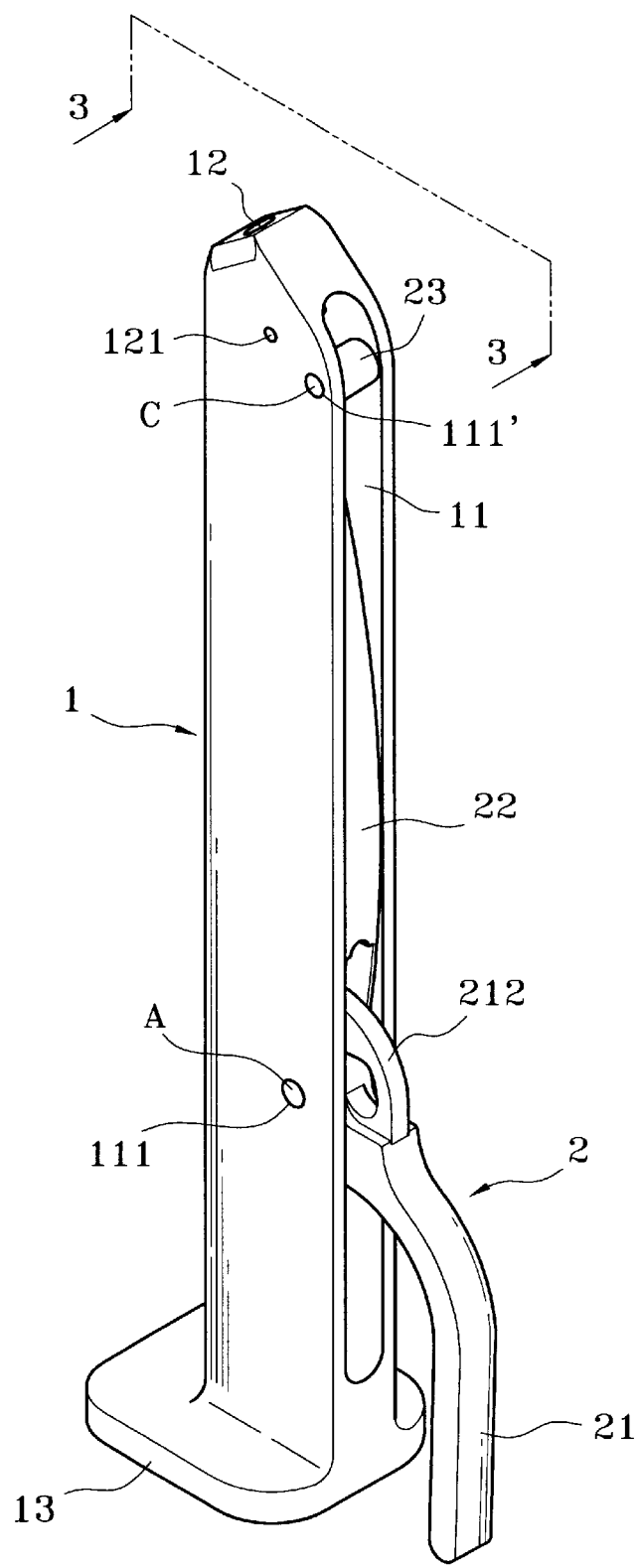
FIG. 1 is a perspective view of the present invention.
Figure 2:
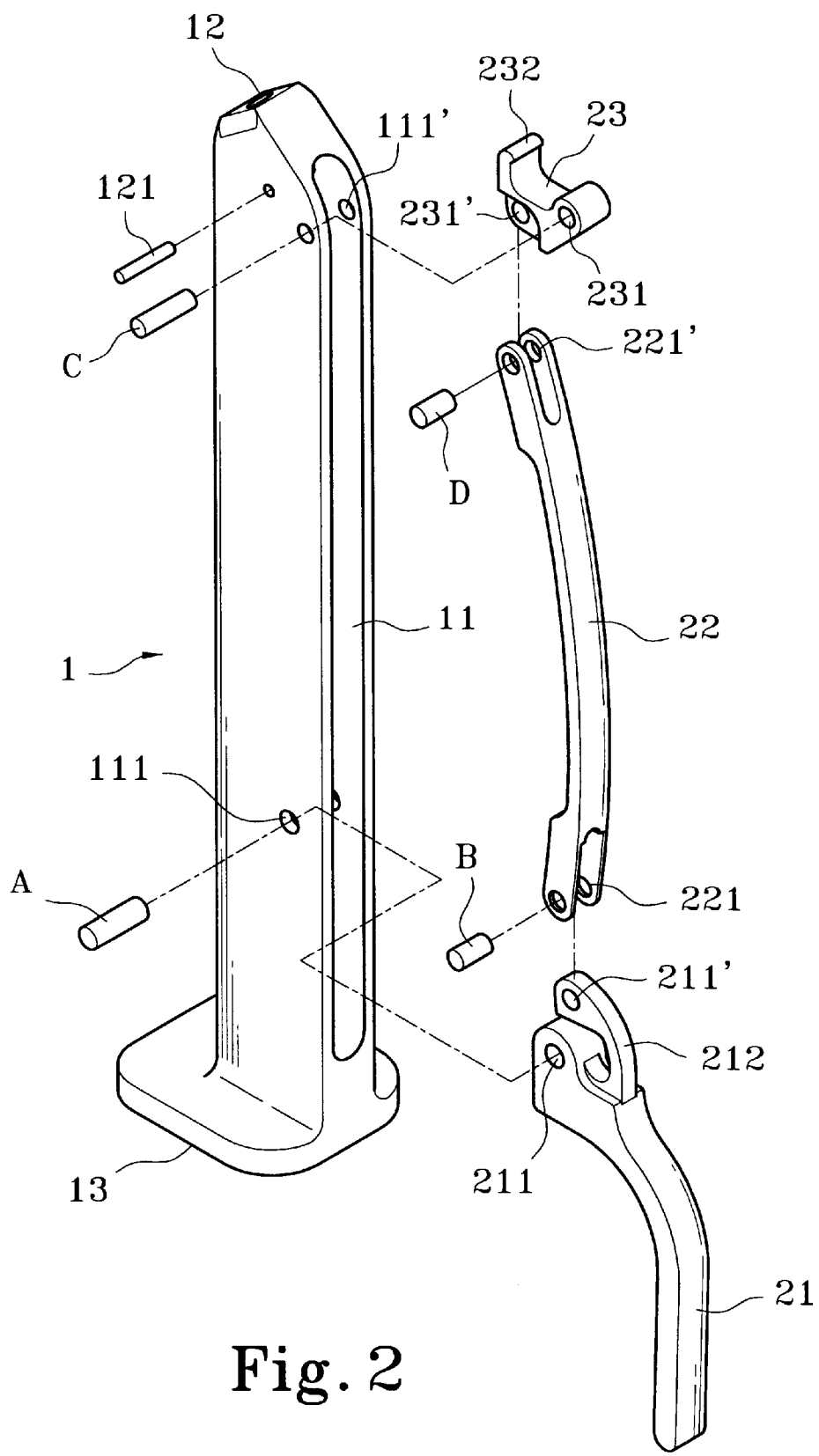
FIG. 2 is an exploded view of the present invention.
Figure 3:
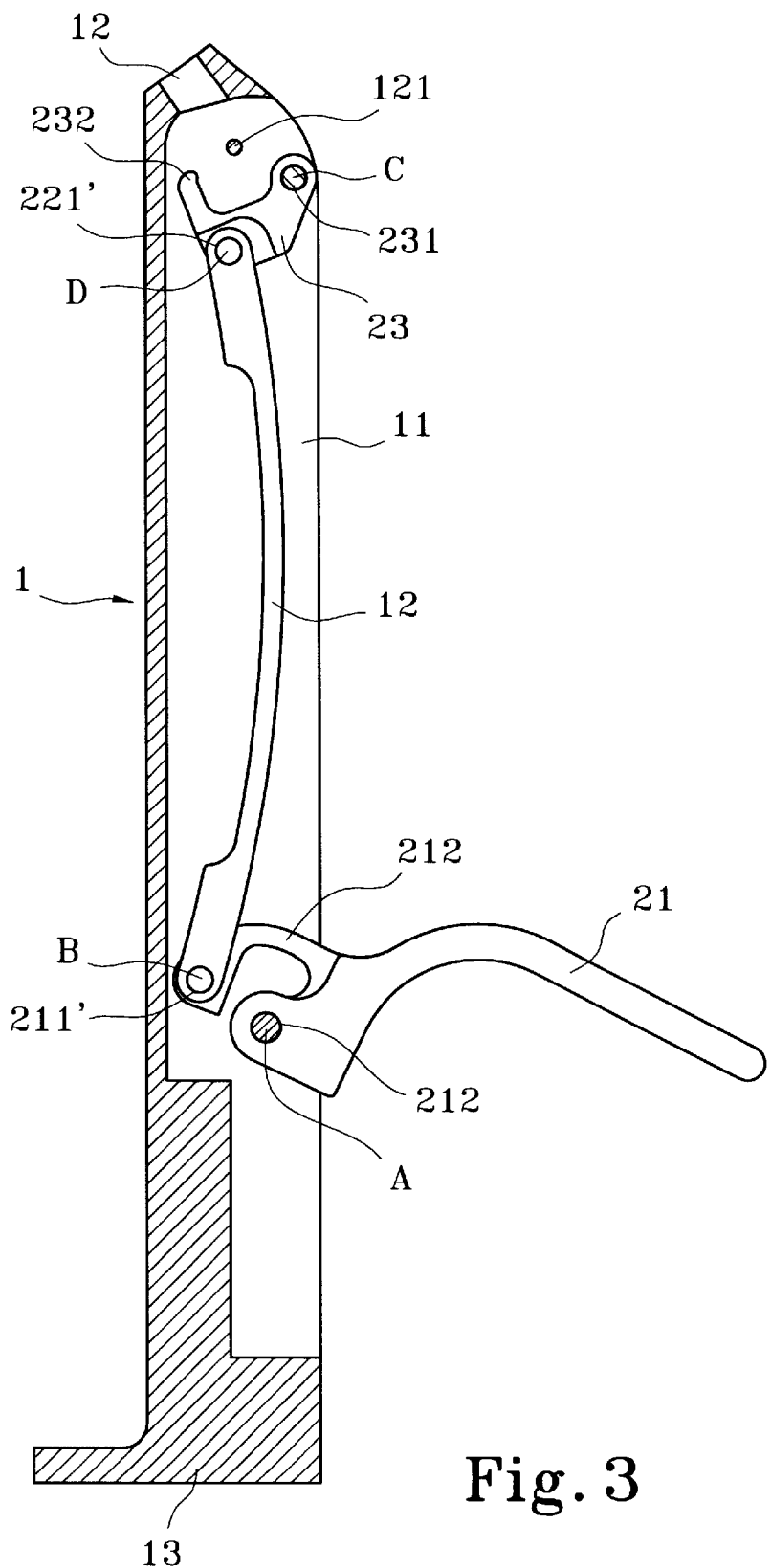
FIG. 3 is a sectional view taking along 3—3 in FIG. 1.

The present invention will become more fully understood from the detailed description given hereinbelow and the accompanying drawings which are given by way of illustration only, and thus are not limitative of the present invention, and wherein:

Referring to FIGS. 1, 2 and 3, the improved femur rasp fastener of the invention consists of a frame 1 and a linkage means 2. The frame 1 has a chamber 11 formed therein to house the linkage means 2 and a front end having an anchor opening 12 formed therein leading to the chamber 11. The anchor opening 12 has a stop pin 121 located therein to buck against the femur rasp (not shown in the drawings). The chamber 11 has two ends each has two side walls forming respectively a pivot section 111 and 111'. The frame 1 has another end formed a hitting section 13.

The linkage means 2 includes a handle 21 which has a pivot head 211 pivotally engageable with the pivot section 111 of the frame 1 through a pivot shaft A. The pivot head 211 has one side extended to form an arched and slightly elastic fulcrum arm 212 which has a pivot section 211' formed at one end thereof. An arched and slightly elastic suspension bar 22 is provided which has a pivot section 221 located at one end pivotally engaging with the pivot section 211' of the fulcrum arm 212 through a pivot shaft B. The suspension bar 22 has another end formed another pivot section 221'. A bucking head 23 is provided which has two pivot sections 231 and 231'. The pivot section 231 is pivotally engaged with the pivot section 111' of the frame 1 through a pivot shaft C. Another pivot section 231' is pivotally engaged with the pivot section 221' of the suspension bar 22 through a pivot shaft D. The bucking head 23 further has one end extended to form a protrusive bucking jut 232 engageable with a femur rasp (not shown in the drawings).

Figure 4:
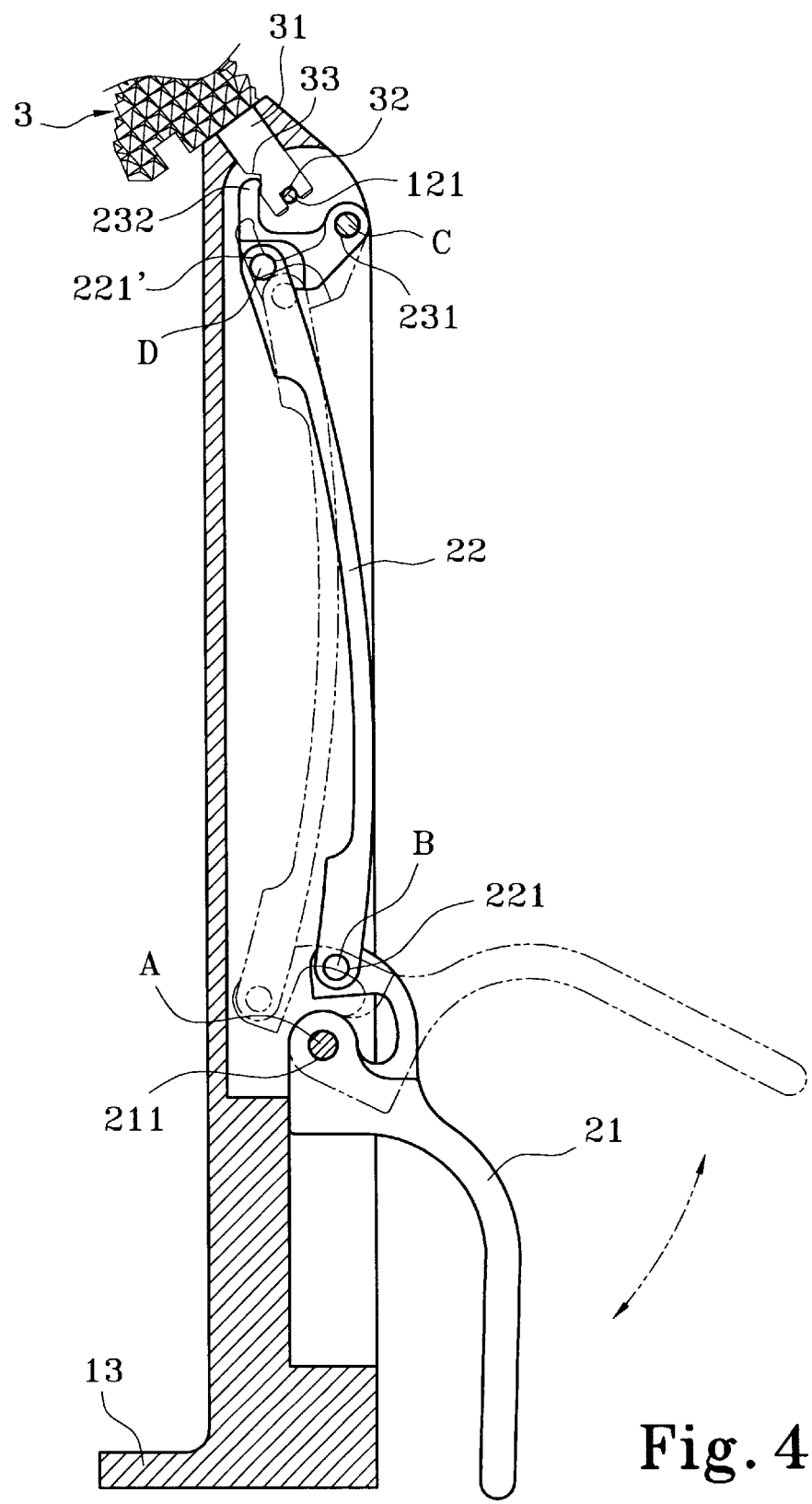
FIG. 4 is a schematic view of the present invention in use.

Referring to FIG. 4, when the fastener of the invention is in use for clamping a femur rasp 3, first move the handle 21 upward to retract the bucking head 23 by means of the suspension bar 22 through the pivotal engagement relationships. Then insert the fasten strut 31 of the femur rasp 3 into the anchor opening 12 and engage the notch 32 at the front end of the strut 31 with the stop pin 121. Then move the handle 21 in the opposite direction to move the suspension bar 22 forward which in turn moves the bucking head 23 forward such that the bucking jut 232 snapping into an indented recess 33 formed in the strut 31. The bucking jut 232 firmly clamps the strut 31 at the indented recess 33 so that the fastener will clamp the femur rasp 3 securely. As the clamping and fastening of the strut 31 and the femur rasp 3 is accomplished, the gap that might take place due to instantaneous vibration will be offset and compensated. Hence the femur rasp 3 will be held and fastened by the frame 1 continuously and securely. The handle 21 may also be positioned securely without loosening off. Even in the event that the hitting section 13 of the frame is hit by doctors during operation, the femur rasp 3 will still be held securely by the frame 1 without loosening off or breaking away.

Once the femur rasp 3 is planted into the marrow, pull the handle 21 upward, the bucking jut 232 of the bucking head 23 may be disengaged from the indented recess 33 of the strut 31, then the femur rasp 3 may be separated from the frame 1.

The improved femur rasp fastener of the invention employs a bucking head located at the front end of a linkage means to snap and clamp the indented recess of a strut located at one end of the femur rasp, and fastens the femur rasp with an elastic stretching force. Such a construction can provide compensation effect to offset the gap resulting from instantaneous vibration. Thus the femur rasp will be clamped securely by the fastener without loosening off or breaking away even when the fastener is hit by the doctors during operations.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A femur rasp fastener for clamping a femur rasp securely, comprising:

a frame for clamping the femur rasp having a chamber formed therein, one end having an anchor opening formed therein leading to the chamber and another end forming a hitting section, the chamber having two side walls formed respectively with a pivot section at two ends thereof; and linkage means housed in the chamber including a handle which has a pivot head pivotally engaging with the pivot section of the frame, the pivot head having an arched fulcrum arm which has one end pivotally engaged with one end of a suspension bar, the suspension bar having another end pivotally engaged with a bucking head which is also pivotally engaging with another pivot section of the frame, the anchor opening includes a stop pin for positioning the femur rasp.

2. The femur rasp fastener of claim 1, wherein the frame has a hitting section located at one end thereof.

3. The femur rasp fastener of claim 1, wherein the fulcrum arm is elastic.

4. The femur rasp fastener of claim 1, wherein the arched suspension bar is elastic.

5. The femur rasp fastener of claim 1, wherein the bucking head has a protrusive bucking jut to clamp the femur rasp.

* * * * *